(12) United States Patent
Koura

(10) Patent No.: US 12,193,673 B2
(45) Date of Patent: Jan. 14, 2025

(54) CLIP DISPENSER AND METHOD FOR DISPENSING AND APPLYING CLIPS TO TISSUE

(71) Applicant: Dravid Koura, Camarillo, CA (US)

(72) Inventor: Dravid Koura, Camarillo, CA (US)

(*) Notice: Subject to any disclaimer, the term of this patent is extended or adjusted under 35 U.S.C. 154(b) by 723 days.

(21) Appl. No.: 17/186,363

(22) Filed: Feb. 26, 2021

(65) Prior Publication Data
US 2021/0380614 A1    Dec. 9, 2021

(51) Int. Cl.
| | | |
|---|---|---|
| A61B 17/10 | (2006.01) | |
| A61B 17/08 | (2006.01) | |
| C12P 13/00 | (2006.01) | |
| A61B 17/29 | (2006.01) | |
| C07F 9/72 | (2006.01) | |

(52) U.S. Cl.
CPC ............ *A61B 17/083* (2013.01); *A61B 17/10* (2013.01); *C12P 13/001* (2013.01); *A61B 17/29* (2013.01); *C07F 9/72* (2013.01)

(58) Field of Classification Search
CPC . A61B 17/122; A61B 17/128; A61B 17/1285; A61B 17/0643; A61B 17/1222; A61B 17/105; A61B 17/08; A61B 17/1227; A61B 2017/0053; A61B 17/2909; A61B 17/29; A61B 17/10; A61B 17/12; A61B 17/068; A61B 2017/00367; A61B 2017/0046; A61B 2017/00473; A61B 2017/00845; A61B 2017/2902; A61B 2017/2939; A61B 2017/2946

See application file for complete search history.

(56) References Cited

U.S. PATENT DOCUMENTS

| | | | |
|---|---|---|---|
| 5,431,669 A | | 7/1995 | Thompson et al. |
| 5,487,746 A | | 1/1996 | Yu et al. |
| 5,591,178 A | | 1/1997 | Green et al. |
| 6,152,936 A | * | 11/2000 | Christy ............ A61B 17/12013 606/139 |
| 6,277,131 B1 | | 8/2001 | Kalikow |
| 6,599,298 B1 | | 7/2003 | Forster et al. |
| 6,863,675 B2 | | 3/2005 | Wilson, Jr. |
| 7,125,403 B2 | | 10/2006 | Julian et al. |

(Continued)

OTHER PUBLICATIONS

Concentric Definition & Meaning—Merriam-Webster (Year: 2023).*
Elongated—Oxford English Dictionary (Year: 2023).*
Concentric Definition—Merriam Webster (Year: 2024).*

*Primary Examiner* — Mohamed G Gabr
*Assistant Examiner* — Aman Kumar Mann
(74) *Attorney, Agent, or Firm* — Williams Intellectual Pro; Tim Snyder

(57) ABSTRACT

A clip dispensing system, clip dispenser, and method is described herein for dispensing and applying clips to tissue during minimally invasive surgery. The system may include a grasping surgical instrument having a shaft and a grasping tool, and a clip dispenser assembled to the shaft. The clip dispenser includes an inner tube surrounded by an outer tube and a plurality of clips housed between the inner tube and the outer tube. The clips include a first jaw, an opposing second jaw, and a cavity between the first jaw and the second jaw. The cavity permits the clip to slide along the length of the shaft and over the grasping tool of the grasping surgical instrument to be clamped onto a grasped piece of tissue with the aid of a second grasping instrument.

12 Claims, 6 Drawing Sheets

(56) References Cited

U.S. PATENT DOCUMENTS

| | | | |
|---|---|---|---|
| 10,368,875 B2 | 8/2019 | Scholten et al. | |
| 10,383,637 B2 | 8/2019 | Castro | |
| 2002/0120254 A1 | 8/2002 | Julian et al. | |
| 2005/0267529 A1* | 12/2005 | Crockett | A61B 17/0643 606/215 |
| 2009/0143789 A1* | 6/2009 | Houser | A61B 17/0057 606/151 |
| 2009/0182282 A1* | 7/2009 | Okihisa | A61B 17/3423 604/165.01 |
| 2010/0174150 A1* | 7/2010 | Park | A61B 17/0218 600/218 |
| 2010/0204717 A1 | 8/2010 | Knodel | |
| 2011/0295281 A1* | 12/2011 | Mizumoto | A61B 17/083 606/151 |
| 2014/0309686 A1* | 10/2014 | Ginn | A61B 17/083 606/216 |
| 2015/0209036 A1 | 7/2015 | Hart | |
| 2015/0265281 A1* | 9/2015 | Hawkins | A61B 17/1285 606/142 |
| 2015/0374392 A1* | 12/2015 | Khan | A61B 17/08 606/113 |
| 2017/0238936 A1 | 8/2017 | Mujawar | |
| 2017/0340331 A1 | 11/2017 | Hu et al. | |
| 2018/0116669 A1* | 5/2018 | Roundy | A61B 17/122 |
| 2019/0053805 A1* | 2/2019 | Harris | A61B 17/10 |
| 2019/0125360 A1 | 5/2019 | Shelton, IV et al. | |
| 2020/0397445 A1* | 12/2020 | Shikhman | A61B 17/1285 |

\* cited by examiner

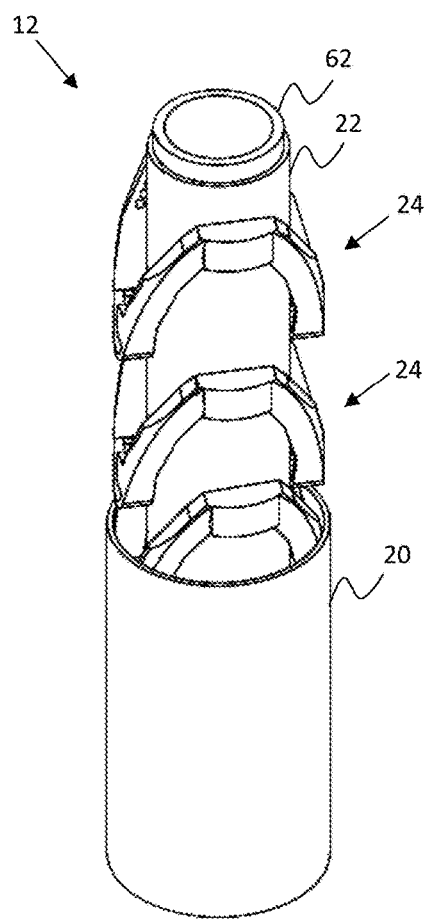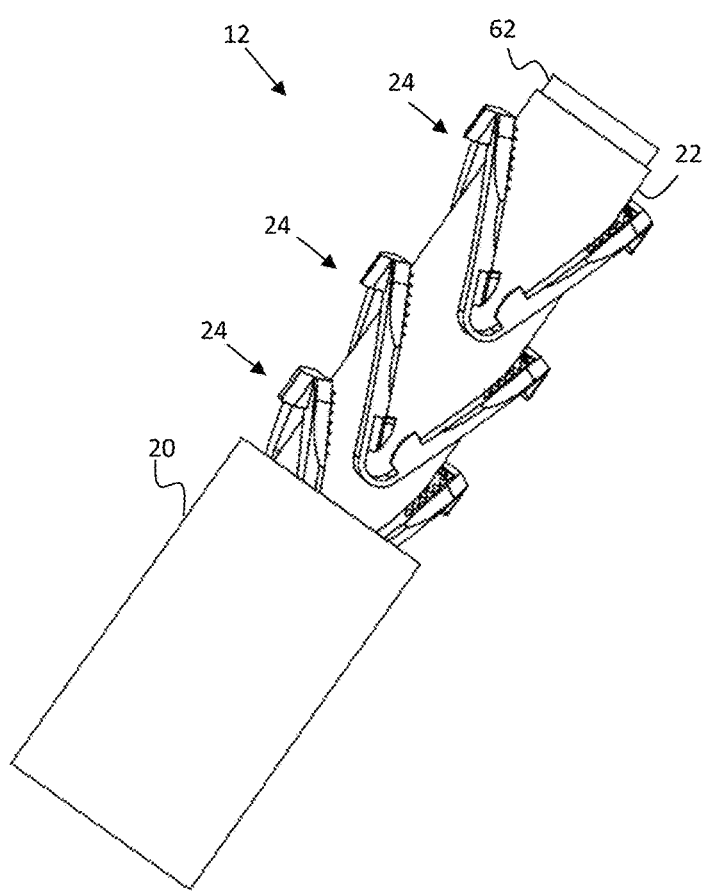
FIG. 3A
FIG. 3B

CLIP DISPENSER AND METHOD FOR DISPENSING AND APPLYING CLIPS TO TISSUE

BACKGROUND OF THE INVENTION

Various systems, devices, and methods for applying clips to tissue during surgery are known in the prior art. However, these systems and devices lack the ability to easily access and apply the clips within a bodily cavity during minimally invasive surgery (MIS). Many minimally invasive soft tissue surgical procedures use different instruments inserted through small ports to access various organs or tissues within a patient's body. Clips are regularly applied to tissues during MIS for various reasons. Current methods to apply a clip to tissue may require a surgeon to remove an instrument (e.g., laparoscopic grasper) from a port and replace it with a clip applicator, or the surgeon may have to utilize a second port for the clip applicator which could otherwise be used for a more effective instrument for the task at hand. This has several disadvantages including increasing the overall surgical time, increasing the rates of infection by having to introduce additional instruments into the cavity, as well as being inefficient from a usability perspective.

Thus there exists a need for a clip dispensing system, clip dispenser, and method for dispensing and applying clips to tissue during minimal invasive surgery in an effective and efficient manner to overcome the aforementioned issues. There further exits a need to easily dispense and clamp a clip on a desired region of tissue from within a bodily cavity.

FIELD OF THE INVENTION

The present invention generally relates to tissue clip applicators for surgery, and more particularly to a clip dispensing system, clip dispenser, and method for dispensing and applying clips to tissue from within a bodily cavity during minimally invasive surgery.

SUMMARY OF THE INVENTION

The general purpose of the clip dispensing system, clip dispenser, and method for dispensing and applying clips to tissue during minimally invasive surgery (MIS) described subsequently in greater detail, is to provide a clip dispensing system, clip dispenser, and method which has many novel features which is not anticipated, rendered obvious, suggested, or even implied by prior art, either alone or in combination thereof.

A clip dispensing system is described herein. The system includes a grasping surgical instrument having a shaft and a grasping tool, and a clip dispenser assembled with the shaft proximal to the grasping tool. The clip dispenser includes an inner tube surrounded by an outer tube, and a plurality of clips housed between the inner tube and the outer tube. The inner tube and outer tube are concentric with the shaft. Each clip of the plurality of clips includes a first jaw, a second jaw, and a cavity between the first jaw and the second jaw. The cavity receives the inner tube therethrough and permits each clip to slide along a length of the shaft and over the grasping tool to be clamped onto a grasped piece of tissue.

A clip dispenser is also described herein for dispensing clips while assembled to a grasping surgical instrument. The clip dispenser includes an inner tube surrounded by an outer tube, and a plurality of clips housed between the inner tube and the outer tube. The inner tube is concentric with the outer tube and configured to concentrically assemble with a shaft of a grasping surgical instrument. Each clip of the plurality of clips includes a first jaw, a second jaw, and a cavity between the first jaw and the second jaw. The cavity receives the inner tube therethrough and permits each clip to slide along a length of the inner tube in the clip dispenser.

A method for dispensing and applying clips to tissue is also described herein. The method uses a first grasping instrument and a second grasping instrument, where the first grasping instrument comprises a shaft, a grasping tool, and a clip dispenser assembled to the shaft proximal to the grasping tool. The method includes grasping a piece of tissue with the first grasping instrument. Grabbing a clip from the clip dispenser with the second grasping instrument. Positioning the clip on the grasped piece of tissue, with the second grasping instrument, by pulling the clip down the shaft and over the grasping tool of the first grasping instrument. The clip is then clamped onto tissue with the second grasping instrument.

Thus has been broadly outlined the more important embodiments of the present invention so that the detailed description thereof that follows may be better understood and in order that the present contribution to the art may be better appreciated.

Embodiments of the present invention, along with various novel features that characterize the invention are particularly pointed out in the claims forming a part of this disclosure. For a better understanding of embodiments of the present invention, and its operating advantages attained by its uses, refer to the accompanying drawings and description.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

FIG. 2A depicts a perspective view thereof, FIG. 2B depicts a top view thereof, FIG. 2C depicts a side view thereof, and FIG. 2D depicts a semi-transparent front view thereof.

FIGS. 3A and 3B depict exploded views of a clip dispenser for storing a plurality of clips therein in accordance with embodiments of the invention, where FIG. 3A is a front perspective view thereof, and FIG. 3B is a side perspective view thereof.

FIG. 6 is a side view thereof, and FIG. 7 is a transverse cross-section showing a variable locking mechanism of the clip in an interlocked configuration.

DETAILED DESCRIPTION OF THE DRAWINGS

Figure 1:
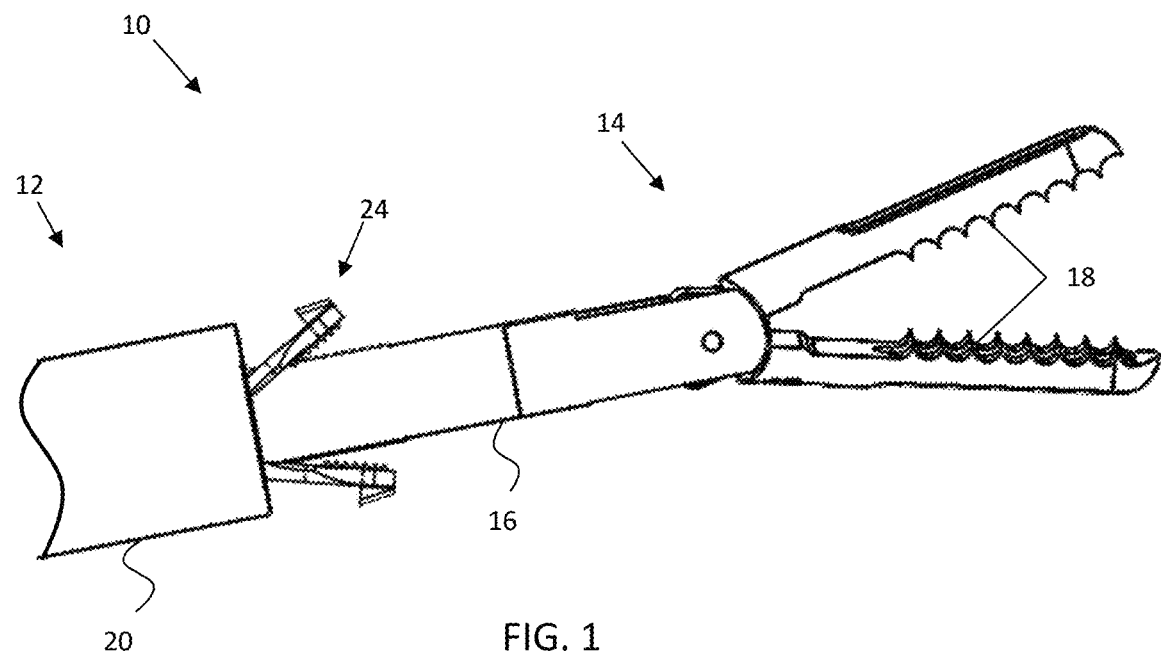
FIG. 1 depicts a system for dispensing one or more clips onto tissue, where the system includes a clip dispenser assembled to the shaft of a laparoscopic grasper in accordance with embodiments of the invention.

The present invention has utility as a system, device, and method for dispensing and applying clips to tissue during minimally invasive surgery in an effective and efficient manner. The present invention is particularly advantageous from a usability perspective. A user can simply apply/clip a clip to desired piece of tissue without having to change instruments or removing instruments from within a bodily cavity. Overall, the present invention may result in decreased surgical times, decreased rates of infection, as well as offering a user-friendly technique for applying clips to tissue.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

Embodiments of the present invention describe a clip dispensing system, a clip dispenser, and a method for dispensing and applying clips to tissue during minimally invasive surgery. The clip dispensing system may include a clip dispenser assembled to a minimally invasive grasping instrument, such as endoscopic forceps. The clip dispenser is configured to dispense a plurality of clips stored therein. The grasping instrument may generally include a shaft and a grasping tool (e.g., forceps) at a distal end of the shaft. The clip dispenser may be concentrically assembled to the shaft of the grasping instrument, where the clips are configured to be pulled down the shaft and over the grasping tool to be applied to tissue grasped by the grasping tool. The method may include the following steps. A first grasping instrument is provided having a shaft, a grasping tool, and a clip dispenser assembled to the shaft, where the clip dispenser includes a plurality of clips housed in the clip dispenser. A desired piece of tissue to be clipped is grasped by the grasping tool of the first grasping instrument. A clip within the clip dispenser is grasped by a second grasping instrument and pulled down along the shaft of the first grasping instrument and positioned onto the grasped piece of tissue. The second grasping instrument then clamps the clip onto the grasped piece of tissue to complete the procedure. Specific embodiments of the clip dispensing system, the clip dispenser, and the method are further described below with reference to the drawings.

With reference now to the figures, FIG. 1 depicts an embodiment of a clip dispensing system 10. The clip dispensing system 10 generally includes a clip dispenser 12 assembled with a minimally invasive grasping instrument 14 (referred to hereinafter as a grasper). The grasper 14 generally includes a shaft 16 and a grasping tool 18 at a distal end of the shaft 16, and may additionally include a proximal end with mechanisms (e.g., handles, levers, triggers, a robot) for controlling the grasper 14 typical of conventional laparoscopic/endoscopic instruments. The grasping tool 18 may be a pair of jaws or forceps for grasping tissue, sutures, or other objects. The clip dispenser 12 may generally include an outer tube 20, an inner tube 22 (shown in FIGS. 3A and 3B), and a plurality of clips 24 stored between the outer tube 20 and inner tube 22. The outer tube 20 and inner tube 22 may be cylindrically shaped to concentrically assemble with the shaft 16 (also having a circular cross-section). Preferably, the clip dispenser 12 is assembled to the shaft 16 in proximity to the grasping tool 18 such that the clip dispenser 12 resides within the bodily cavity during the surgical operation.

Figure 2A:
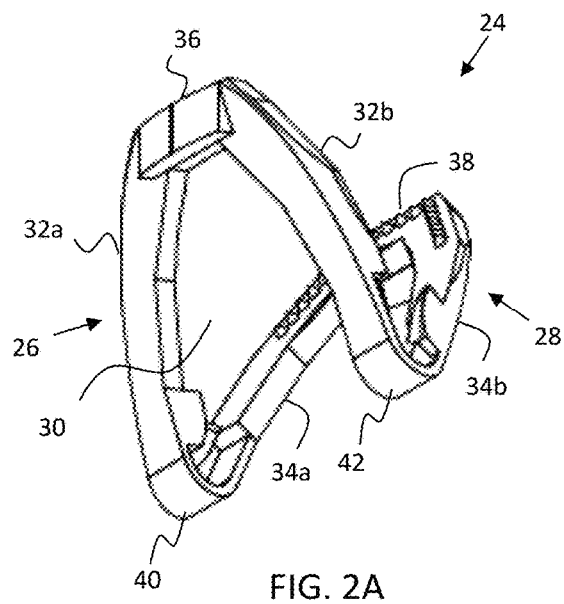
FIGS. 2A to 2D depict a clip storable inside a clip dispenser and appliable to tissue in accordance with embodiments of the invention, where
Figure 2B:
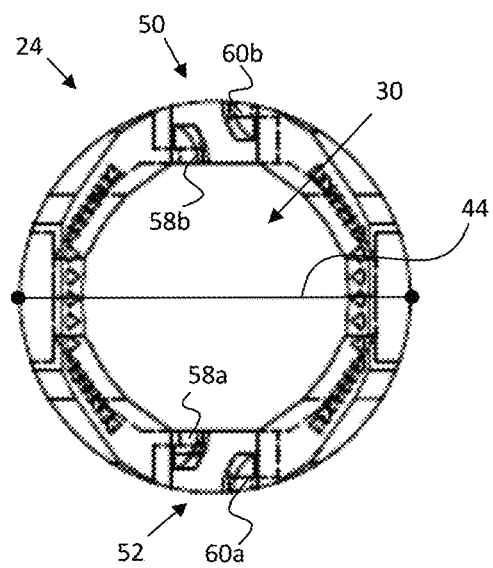
Figure 2C:
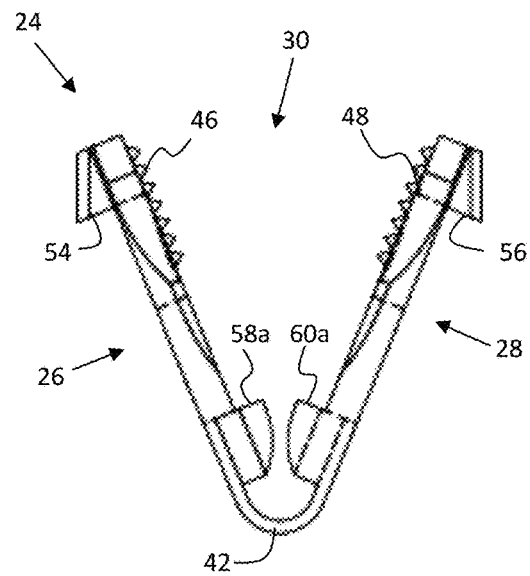
Figure 2D:
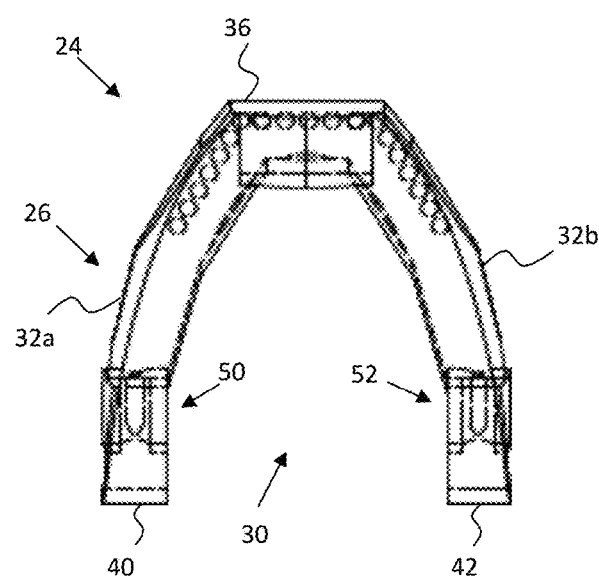

With reference to FIGS. 2A to 2D, embodiments of a clip 24 housed in the clip dispenser 12 and appliable to tissue is shown. The clip 24 generally includes a first jaw 26 and an opposing second jaw 28 designed to clamp onto tissue. The clip 24 further includes a cavity 30 in which the inner tube 22 and/or shaft 16 fit through to permit the clip 24 to be housed in the clip dispenser 12, and to allow the clip 24 to slide along the inner tube 22 and the shaft 16. In particular embodiments, each jaw (26, 28) is in the general shape of a 'U' or 'V' having a distal end (36, 38), and a pair of legs (32a, 32b, 34a, 34b) extending from the distal end (36, 38). The shape of the distal ends (36, 38) may be flat (as shown), pointed (consistent with a 'V' shape), or rounded (consistent with a 'U' shape). Each pair of legs (32a and 32b, or 34a and 34b) may extend in a convergent, parallel, or divergent manner, or a combination thereof. FIGS. 2A to 2D depict each pair of legs (e.g., 32a and 32b) being initially divergent relative to each other (starting from the distal end 36) and ending in a parallel configuration. Each pair of legs (32a and 32b, and 34a and 34b) have a proximal end to facilitate the connection of the first jaw 26 with the second jaw 28. More specifically, the proximal end of each leg (32a, 32b) of the first jaw 26 join or meet with a corresponding proximal end of each leg (34a, 34b) of the second jaw 28 to form a pair of pivot points (40, 42). That is, the proximal ends of legs 32a and 34a join to form pivot point 40, and the proximal ends of legs 32b and 34b join to form pivot point 42. The pivot points (40, 42) may likewise be in the shape of a 'U' or 'V', such that the overall shape of the clip 12 has a lateral cross-section in the shape of a 'U' or 'V' as best shown in FIG. 2C. This is particularly advantageous for housing multiple clips 24 in the clip dispenser 12, and minimizing the overall diameter of the clip dispenser 12 to fit through surgical ports.

The cavity 30 that the inner tube 22 and shaft 16 fit through may be formed by the empty space between the legs (32a, 32b, 34a, 34b), the distal ends (36, 38), and the pivot points (40, 42). The overall shape of the clips 24 may therefore resemble the boney structure of shark jaws, where the inner tube 22 and shaft 16 would fit through the space between the shark jaws. The clip 24 may further have an outer circular profile (as best seen in FIG. 2B) to permit the clips 24 to fit concentrically in the clip dispenser 12 and/or concentric with the shaft 16. In other words, the outer edges of a transverse cross-section of the clip 24 are curved to match (in shape) with the cylindrical shape of the outer tube 20 of the clip dispenser 12. Here, a transverse cross-section refers to a cross-section that cuts through the clip 24 anywhere between the distal ends (36, 38) and the pivot points (40, 42) of the clip 24. The diameter of the outer circular profile is represented as the bounded line 44 in FIG. 2B, and has a diameter that is 0.1% to 20% smaller than the inner diameter of the outer tube 20.

The clip 24 may further include teeth (46, 48), locking mechanisms (50, 52), and protrusions (54, 56). The teeth (46, 48) may be disposed on interior surfaces of the first jaw 26 and the second jaw 28 to grasp on tissue when clamped thereon. In particular embodiments, teeth (46, 48) are disposed on the distal ends (36, 38), and on distal regions of the legs (32a, 32b, 34a, 34c) as best seen in FIG. 2C. The locking mechanisms (50, 52) are configured to lock the clip 24 in a clamped position. This prevents the clip 23 from opening or coming loose when clamped onto tissue. The locking mechanisms (50, 52) may include locking components (58a, 58b, 60a, 60b) disposed on interior surfaces of the first jaw 26 and the second jaw 28. In particular embodiments, the locking components (58a, 58b, 60a, 60b) are disposed at a proximal region of the legs (32a, 32b, 34a, 34b) and interlock with one another to lock the clip 24 in the clamped position. For example, the first jaw 26 may have a first locking component 58a on a first leg 32a and a second locking component 58b on a second leg 32b, and the second jaw 28 may having a first locking component 60a on a leg 34a and a second locking component 60b on a second leg 34b, such that when the clip 24 is closed, the first locking components (58a, 60a) interlock together and the second locking components (58b 60b) interlock together to secure the clip 24 in the clamped position. The locking components (58a, 58b, 60a, 60b) may illustratively include interlocking hooks, latches, clasps, clips, and snaps. The protrusions (54, 56) are configured to assist a second grasping instrument with holding, positioning, or handling the clip 24 when dispensing, positioning, and/or clamping the clip 24 onto tissue. In particular, the protrusions (54, 56) may stop a second grasper 14' (FIG. 4) from slipping from the clip 24 when positioning or clamping the clip 24 onto tissue. The protrusion (54, 56) may be disposed on an exterior surface of the distal ends (36, 38) of the clip 24 and project exteriorly therefrom. In particular embodiments, the protrusions (54, 56) are triangular in form having a flat proximal surface that the second grasper can abut against and/or stop against while positioning the clip 24 onto tissue. This prevents the second grasper 14' from slipping over the distal end of the clip 24 and may further provide a surface to pull against to position the clip 24. It should be appreciated that other shapes may exteriorly project from the distal ends (36, 38) that likewise provide an abutment surface to prevent a second grasper 14' from slipping over the distal ends (36, 38) of the clip 24.

With reference to FIGS. 3A and 3B, an exploded view of a clip dispenser 12 is shown having a plurality of clips 24 housed therein. The clip dispenser 12 generally includes an outer tube 20, an inner tube 22, and a plurality of clips 24. The plurality of clips 24 reside between the outer tube 20 and the inner tube 22, where the inner tube 22 fits through the cavity 30 of the clips 24, and the outer tube 20 surrounds the outer edges of the clips 24. The clip dispenser 12 may further include a grip 62 that fits onto or over the shaft 16 to secure the clip dispenser 12 to the shaft 16. The grip 62 may be, for example, a rubber grip. In particular embodiments, the outer tube 20 spans the whole length of the clip dispenser 12 and has an outer diameter of approximately 10 mm in order to pass through a 10-12 mm trocar.

In some embodiments, the clip dispenser 12 is an individual piece of sterilized surgical equipment that can removably assemble to the shaft 16 in the operating room. Alternatively, the clip dispenser 12 may be fixed and/or manufactured as part of the grasper 14.

Figure 4:
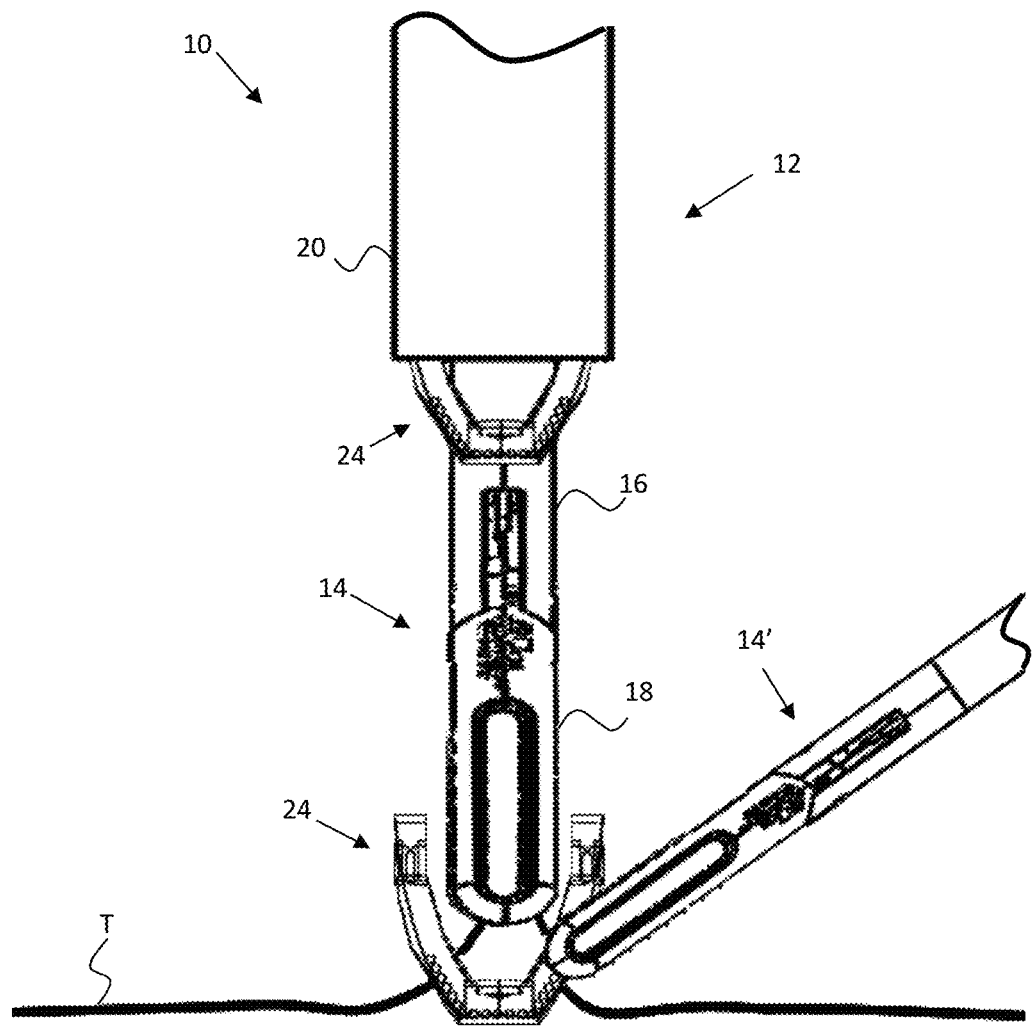
FIG. 4 depicts a system and method for dispensing and applying a clip onto tissue in accordance with embodiments of the invention.

With reference to FIG. 4, a particular embodiment of a method for dispensing and applying a clip 24 to tissue T is shown. The method may include the use of a first grasper 14 having a clip dispenser 12 assembled to the shaft 16 of the first grasper 14, and a second grasping instrument 14' (referred to herein after as a second grasper). The method may begin by grasping a targeted piece of tissue with the first grasper 14. The second grasper 14' then grabs a clip 24 from the clip dispenser 12, pulls the clip 24 down and over the grasping tool 18 of the first grasper 14, and onto the targeted piece of tissue. The second grasper 14' then clamps the clip 24 onto the targeted tissue. All of the above may be performed form within a bodily cavity and provides a user-friendly technique for applying clips to tissue in a minimally invasive manner.

Figure 5:
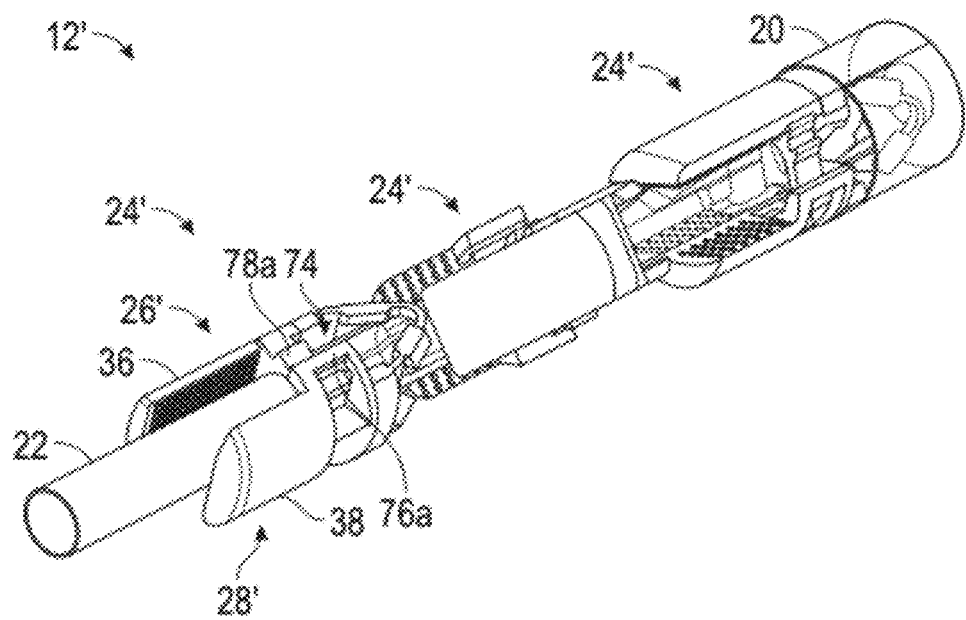
FIG. 5 depicts an exploded perspective view of a clip dispenser and a plurality of variable locking clips in accordance with embodiments of the invention.
Figure 6:
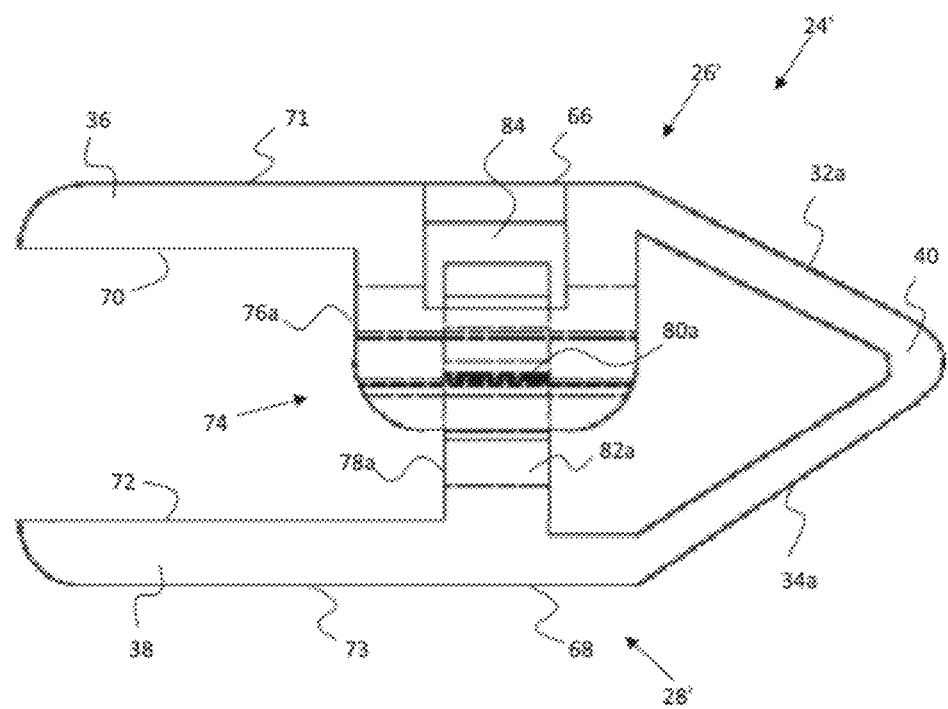
FIGS. 6 and 7 depicts a variable locking clip in accordance with embodiments of the invention, where
Figure 7:
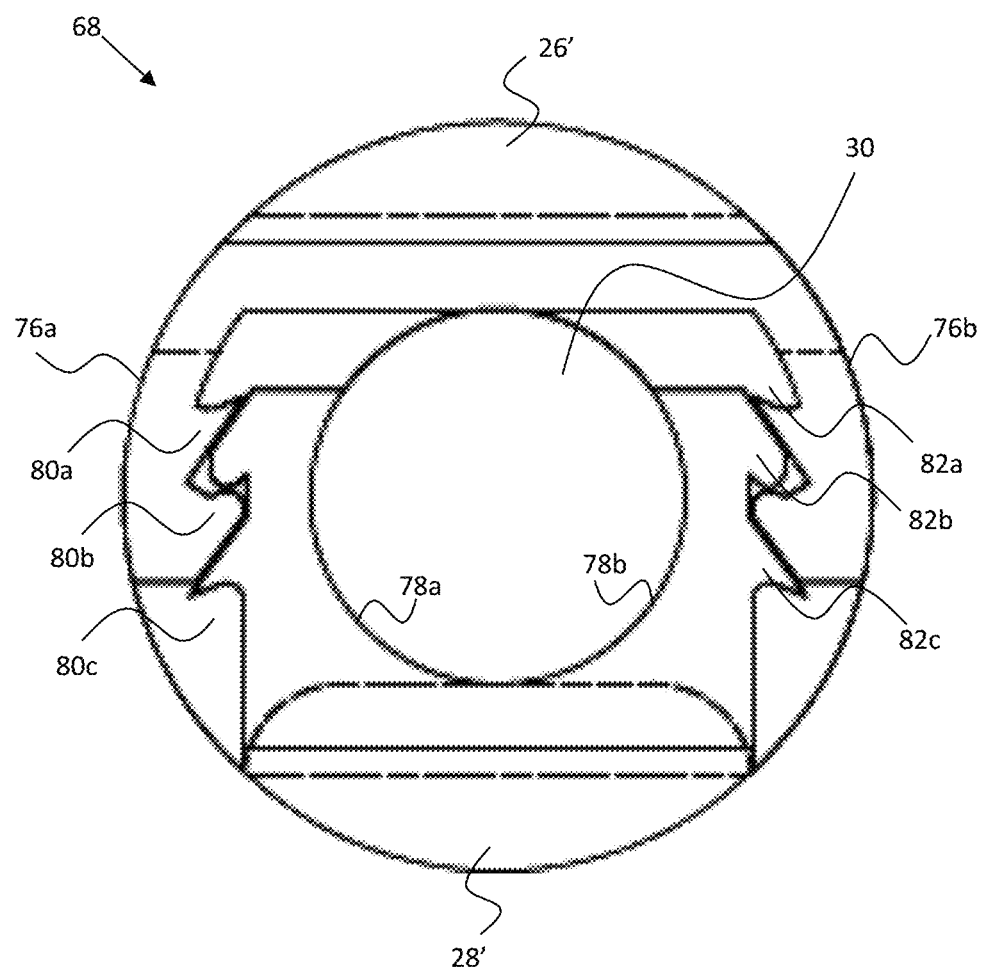

With reference now to FIGS. 5 through 7, a particular embodiment of a clip dispenser 12' is shown for use with the clip dispensing system 10 and method as described above. The clip dispenser 10' likewise includes an outer tube 20, an inner tube 22, and a plurality of clips 24' housed therebetween. FIG. 5 depicts an exploded view of the clips 24' positioned along the length of the inner tube 22. The clips 24' of the clip dispenser 12' are configured with a variable locking mechanism 74 to adjust a level of clamping tightness on the tissue. FIGS. 6 and 7 depict a detailed view of the clips 24' with the variable locking mechanism 74, where FIG. 6 is a side view of thereof, and FIG. 7 shows a transverse cross-section of the variable locking mechanism 74. The clip 24' generally includes a first jaw 26' and an opposing second jaw 28' designed to clamp onto tissue. In particular embodiments, each jaw (26', 28') has a distal end (36, 38) having an interior surface (64, 66) that contacts the tissue when clamped thereon, and an exterior surface (71, 73). The distal ends (36, 38) may be elongated as best seen in FIG. 6 where the distal ends (36, 38) may be the only portion of the clip 24' that clamps onto the tissue. The interior surfaces (64, 66) of the distal ends (36, 38) may be planar or curved in shape. If the surfaces are planar, then the surfaces (64, 66) may be parallel to one another. The interior surfaces (64, 66) may further include a plurality of teeth or stipples (not shown).

The variable locking mechanism 74 of the clips 24' may be designed similar to a zip-tie, where a plurality of protrusions interlock to adjust the tightness of the jaws (26, 28) at regular intervals. The first jaw 26' may include a pair of female locking members (76a, 76b) projecting from opposing sides of the first jaw 26'. The pair of female locking members (76a, 76b) may be disposed at a proximal region 66 of the distal end 36 of the first jaw 26'. The second jaw 28' may include a pair of male locking members (78a, 78b) projecting from opposing sides of the second jaw 28'. Likewise, the male locking members (78a, 78b) may be disposed at a proximal region 68 of the distal end 38 of the second jaw 28' to align with the female locking members (76a, 76b) on the first jaw 26'. Each female locking member (76a, 76b) may include one or more protrusions (80a, 80b, 80c) to interlock with corresponding protrusions (82a, 82b, 82c) on each male locking member (78a, 78b). Each female locking member (76a, 76b) may further include an opening 84 that each male locking member (78a, 78b) fits through to facilitate the interlocking of the protrusions. The opening 84 may further permit a user to visualize a degree of tightness to the clip 24' based on the number of interlocking connections formed between the male locking members (78a, 78b) and female locking members (76a, 76b). The variable locking mechanism 74 enables several levels of tightness, where the tightest level is when the teeth (or stipples) on the interior surfaces (64, 66) are completely flush. In particular embodiments, the clips 24' have three activation/tightening phases. As a precautionary measure, to prevent misfire, the default position of the clip 24' is locked in the first tightening phase (or the interlocking of the first protrusions—least tight position). Pressure exerted on the exterior surfaces (71, 73) of the jaws (26', 28') of the clip 24' (e.g., by a second grasper 14') then activates the second and third tightening levels. It should be appreciated that two, three, or more tightening levels may be achieved by varying the number of protrusions on at least one of the female locking members (76a, 76b) and/or the male locking members (78a, 78b).

The clips 24' may further include legs (32a, 32b, 34a, 34b), pivot points (40, 42), cavity 30, and a circular outer profile as described above with reference to clip 24.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

What is claimed is:

1. A clip dispensing system, comprising:
   a grasping surgical instrument having a shaft and a grasping tool; and
   a clip dispenser assembled with the shaft proximal to the grasping tool, said clip dispenser comprising:
      an inner tube surrounded by an outer tube, and a plurality of clips housed between the inner tube and the outer tube;
      wherein the inner tube and outer tube are concentric with the shaft; and
      wherein each clip of the plurality of clips comprise a first jaw, an opposing second jaw, and a cavity between the first jaw and the second jaw, wherein the inner tube and shaft fits through the cavity and permits each clip to slide along a length of the inner tube and the shaft, and slide over the grasping tool to be clamped onto a grasped piece of tissue; and
   a second grasping instrument comprising a second grasping tool, wherein the second grasping tool is configured to releasably grasp a clip from the plurality of clips, and wherein the second grasping instrument is used to position the clip onto the grasped piece of tissue.

2. The clip dispensing system of claim 1 wherein the clip dispenser is in proximity to the grasping tool such that the clip dispenser resides within a bodily cavity during an operation.

3. The clip dispensing system of claim 1 wherein the first jaw comprises a first distal end and a first pair of legs extending from the first distal end, and the second jaw comprises a second distal end and a second pair of legs extending from the second distal end, wherein each leg from the first pair of legs has a proximal end, and each leg from the second pair of legs has a proximal end, and wherein each proximal end from the first pair of legs meet with a corresponding proximal end from the second pair of legs to form a pair of pivot points.

4. The clip dispensing system of claim 3 wherein the cavity is formed by the space between: a) the first distal end and the second distal end; b) the first pair of legs; c) the second pair of legs; d) the first pair of legs and the second pair of legs; and e) the pair of pivot points.

5. The clip dispensing system of claim 3 wherein each distal end is elongated and comprises an interior surface that contacts the tissue.

6. The clip dispensing system of claim 1 wherein the clip has a cross-section with an outer circular profile.

7. The clip dispensing system of claim 1 wherein the clip further comprises teeth to grasp onto tissue and a locking mechanism to lock the clip in a clamped position.

8. The clip dispensing system of claim 7 wherein the locking mechanism is a variable locking mechanism to adjust a level of clamping tightness on the tissue.

9. The clip dispensing system of claim 1 wherein the clip further comprises a first protrusion disposed on an exterior surface of the first jaw, and a second protrusion disposed on an exterior surface of the second jaw.

10. The clip dispensing system of claim 1 wherein the clip dispenser is removably assembled on the shaft of the grasping surgical instrument.

11. The system of claim 1 wherein the second grasping instrument is independent of the first grasping instrument and is movable in any direction relative to the first grasping instrument.

12. A method for dispensing and applying clips to tissue using a first grasping instrument and a second grasping instrument, wherein the first grasping instrument comprises a shaft, a grasping tool, and a clip dispenser assembled to the shaft, the method comprising:
   grasping a piece of tissue with the first grasping instrument;
   grabbing a clip from the clip dispenser with the second grasping instrument, wherein the clip dispenser comprises:
      an inner tube surrounded by an outer tube, and a plurality of clips housed between the inner tube and the outer tube;
      wherein the inner tube is concentric with the outer tube and configured to concentrically assemble with a shaft of a grasping surgical instrument; and
      wherein each clip of the plurality of clips comprise a first jaw, an opposing second jaw, and a cavity between the first jaw and the second jaw, wherein the cavity receives the inner tube therethrough and permits each clip to slide along a length of the inner tube in the clip dispenser;
   positioning the clip on the grasped piece of tissue, with the second grasping instrument, by pulling the clip down the shaft and over the grasping tool of the first grasping instrument; and
   clamping the clip on the grasped piece of tissue with the second grasping instrument.

* * * * *